(12) United States Patent
Kloster et al.

(10) Patent No.: US 8,875,335 B2
(45) Date of Patent: Nov. 4, 2014

(54) MECHANICALLY DRIVEN RESONANT DRIVE TRAIN FOR A POWER TOOTHBRUSH

(75) Inventors: Tyler G. Kloster, Snoqualmie, WA (US); Wolter F. Benning, Seattle, WA (US); Yu-Wen Chang, Mercer Island, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/513,977

(22) PCT Filed: Nov. 22, 2010

(86) PCT No.: PCT/IB2010/055340
§ 371 (c)(1),
(2), (4) Date: Jun. 5, 2012

(87) PCT Pub. No.: WO2011/077285
PCT Pub. Date: Jun. 30, 2011

(65) Prior Publication Data
US 2012/0284937 A1  Nov. 15, 2012

Related U.S. Application Data

(60) Provisional application No. 61/289,482, filed on Dec. 23, 2009.

(51) Int. Cl.
*A61C 17/34* (2006.01)

(52) U.S. Cl.
CPC ............................ *A61C 17/3418* (2013.01)
USPC ........................................... 15/22.1; 15/22.2

(58) Field of Classification Search
USPC .................... 15/22.1, 167.1, 22.2; 310/80
See application file for complete search history.

(56) References Cited

U.S. PATENT DOCUMENTS

| | | | | |
|---|---|---|---|---|
| 5,261,430 A | * | 11/1993 | Mochel | 132/322 |
| 5,381,576 A | * | 1/1995 | Hwang | 15/22.1 |
| 5,406,664 A | * | 4/1995 | Hukuba | 15/22.1 |
| 6,833,639 B2 | * | 12/2004 | Lau et al. | 310/36 |
| 7,020,925 B1 | * | 4/2006 | Gitelis | 15/22.1 |
| 7,627,922 B2 | * | 12/2009 | Miller et al. | 15/22.1 |
| 7,712,174 B2 | * | 5/2010 | Shimizu et al. | 15/22.1 |
| 7,836,538 B2 | * | 11/2010 | Cobabe et al. | 15/28 |

(Continued)

FOREIGN PATENT DOCUMENTS

| | | |
|---|---|---|
| DE | 102006061381 A1 | 6/2008 |
| EP | 0281974 A1 | 9/1988 |

(Continued)

*Primary Examiner* — Monica Carter
*Assistant Examiner* — Michael Jennings

(57) ABSTRACT

The power toothbrush includes a driving assembly which in turn includes a DC motor (14) and a battery. The DC motor has a rotating drive shaft (16), supported at its free end. The drive shaft has an eccentric portion (18). Mounted on the eccentric portion is a plastic sleeve (20) having an extending portion which engages one end of a spring member (38). The other end of the spring member is secured to a yoke (36) which is secured to a brushhead shaft (32). Rotation of the drive shaft results in the extending portion of the plastic sleeve, moving the spring between a compressed state and an extended state. The action of the DC motor excites the spring to produce an oscillating action of the brushhead shaft and a brushhead assembly (40) mounted thereon.

8 Claims, 4 Drawing Sheets

(56) References Cited

U.S. PATENT DOCUMENTS

| | | | |
|---|---|---|---|
| 7,861,348 B2 * | 1/2011 | Chan | 15/22.1 |
| 8,239,991 B2 * | 8/2012 | Shimizu et al. | 15/22.1 |
| 8,291,537 B2 * | 10/2012 | Gall et al. | 15/22.1 |
| 2002/0178519 A1 * | 12/2002 | Zarlengo | 15/22.2 |
| 2003/0204924 A1 * | 11/2003 | Grez et al. | 15/22.1 |
| 2004/0049868 A1 * | 3/2004 | Ng | 15/22.2 |
| 2004/0261203 A1 * | 12/2004 | Dworzan | 15/22.1 |
| 2007/0011834 A1 * | 1/2007 | Shimizu et al. | 15/22.1 |
| 2007/0151051 A1 * | 7/2007 | Filsouf | 15/22.1 |
| 2007/0214587 A1 * | 9/2007 | Stoeffler et al. | 15/22.1 |
| 2010/0132140 A1 * | 6/2010 | Diamond | 15/22.1 |

FOREIGN PATENT DOCUMENTS

| | | | | |
|---|---|---|---|---|
| EP | 968686 A1 * | 1/2000 | | A61C 17/34 |
| EP | 2018831 A1 | 1/2009 | | |
| EP | 2246009 A1 | 3/2010 | | |
| JP | 09285660 A | 11/1997 | | |
| WO | 2011058465 A1 | 5/2011 | | |

* cited by examiner

MECHANICALLY DRIVEN RESONANT DRIVE TRAIN FOR A POWER TOOTHBRUSH

This invention relates generally to power toothbrushes, and more specifically concerns a drive train for a power toothbrush.

In one form of a drive train for a power toothbrush, a sinusoidal signal is used to drive a spring assembly which in turn drives the portion of the toothbrush in a desired oscillating motion. However, the stators necessary to produce the required sinusoidal signal to create the magnetic field to drive the spring system are custom-made and, combined with the electronics required for such a drive system, substantially increase the overall expense of such a power toothbrush.

Alternatively, DC motors have been used in a power toothbrush drive train for simplicity and to decrease overall expense. In order to produce an oscillating brushhead action, which is generally the most effective for teeth cleaning, a crank arm and linkage has been used with the DC motor to generate the required oscillating brushhead motion and amplitude. As the frequency of the brushhead motion is increased to an effective value, however, the torque requirements for the motor operating with a crank and linkage mechanism increase.

It is hence desirable to have a drive train system which for simplicity and economy uses a DC motor, but does not have the disadvantages of a direct crank and linkage assembly to produce the desired brushhead motion.

Accordingly, the power toothbrush, comprises: a driving assembly, including a battery and a DC motor, the DC motor having a rotating drive shaft extending therefrom, the drive shaft having a free end rotationally mounted in a support member, the drive shaft having an eccentric portion located proximally from the free end thereof; a spring assembly extending from the eccentric portion, the spring assembly including a spring member which alternates between two conditions as the eccentric portion rotates; a brushhead shaft member, wherein the brushhead shaft member has a yoke member secured thereto and extending away therefrom, the yoke member also being secured to the spring member, wherein in operation, an oscillating action of the brushhead shaft is produced as the eccentric portion of the drive shaft rotates, with the spring member alternating between its two conditions; and a brushhead assembly with bristles mounted on the brushhead shaft for cleaning a user's teeth.

Figure 1:
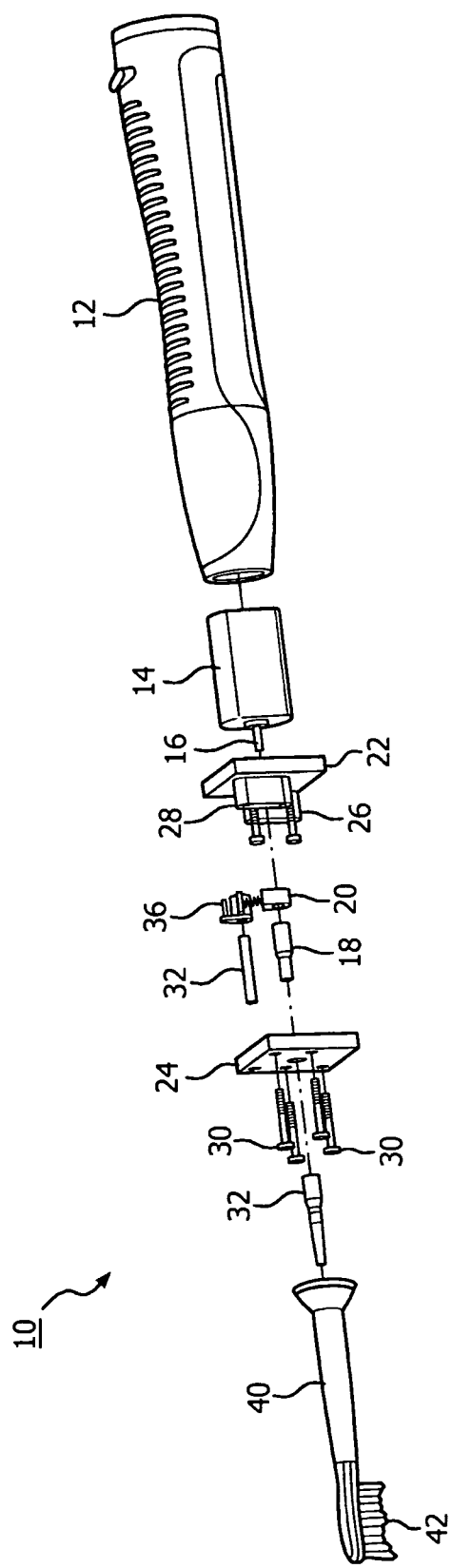
FIG. 1 is an exploded view of the toothbrush with the drive train disclosed herein.
Figure 2:
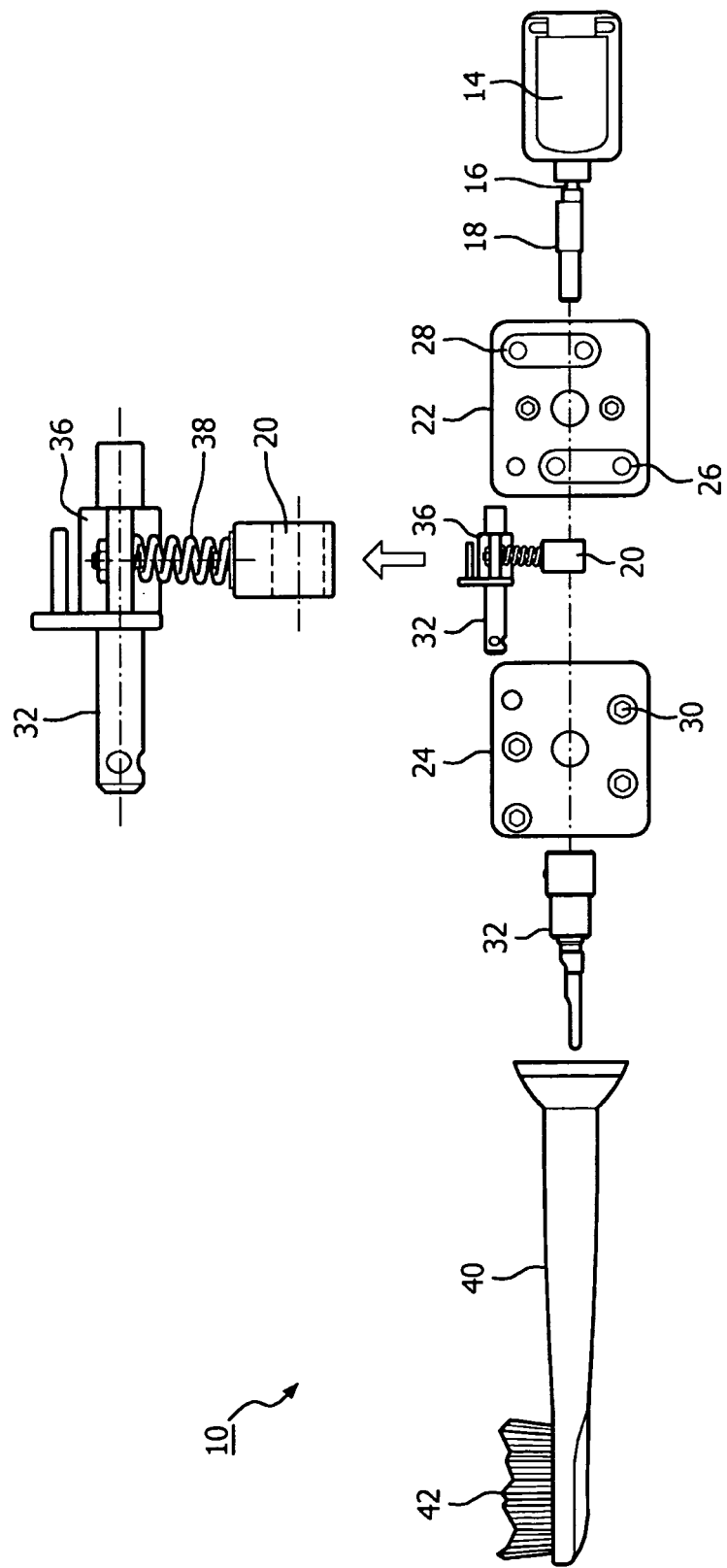
FIG. 2 is another exploded view of the toothbrush.

Referring to FIGS. 1 and 2, a power toothbrush is shown at 10. The toothbrush 10 includes a conventional handle 12 in which is positioned a DC motor 14. In the embodiment shown, the DC motor is high-speed (5K-20K rpm, or approximately 80-320 revolutions per second) and low torque (0.2 milliNewton-meters to 1.5 milliNewton-meters), although these values can be varied. Extending from DC motor 14 is the motor (drive) shaft 16, which includes an eccentric portion 18. The eccentric portion in the embodiment shown is located approximately 8 mm along the shaft 16, is approximately 18 mm long, and has an eccentricity of 0.5 mm. Mounted on eccentric portion 18 is a plastic sleeve 20.

Figure 3:
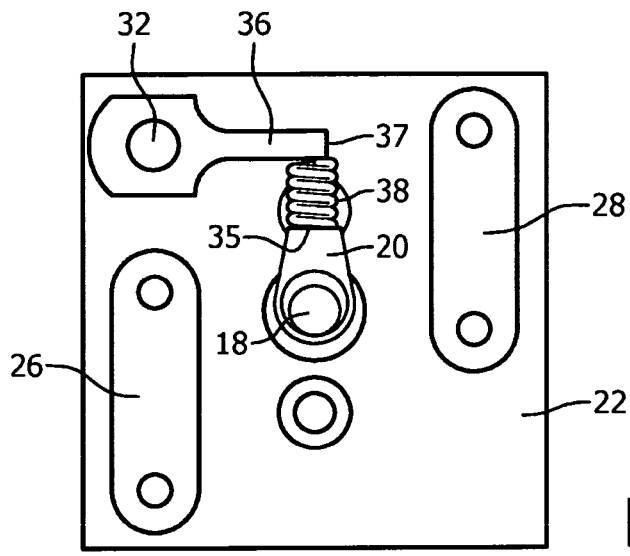
FIG. 3 is a cross-sectional view showing the spring assembly portion of the drive train in compression.
Figure 4:
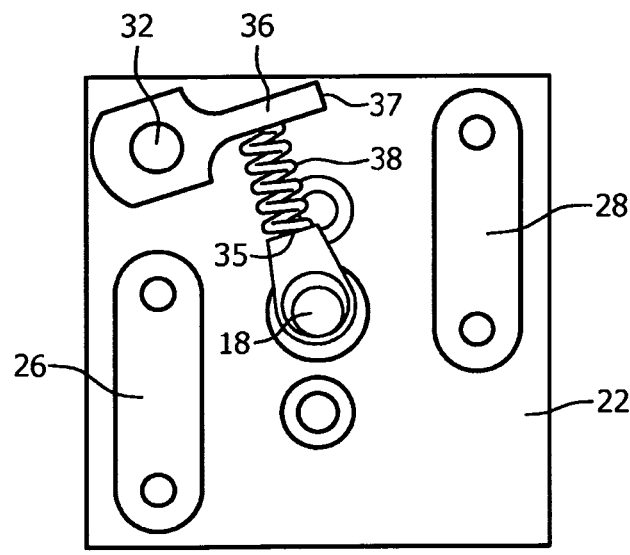
FIG. 4 is a cross-sectional view showing the spring assembly portion in extension.
Figure 5:
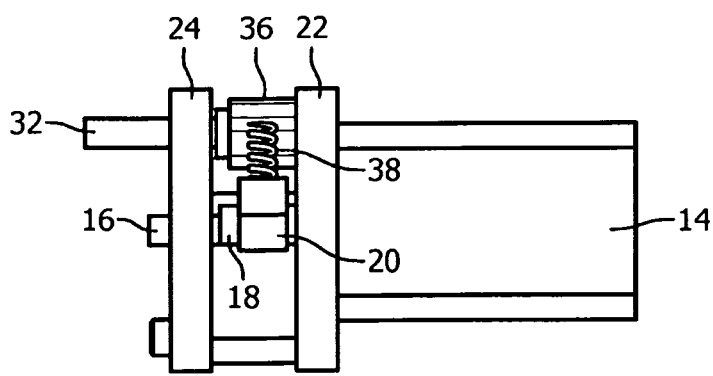
FIG. 5 is a side elevational view showing a portion of the toothbrush of FIGS. 1-4.

Motor shaft 16 extends through an opening in and is supported by a support plate 22 which is proximal to DC motor 14 and which is secured to handle 12 of the toothbrush, such that it does not move. A second support plate 24 in which the distal end of drive shaft 16 is mounted away from support plate 22 in a direction away from motor 14. Positioned between the two support plates 22 and 24 are standoff members 26 and 28. Support plates 22 and 24 and standoff members 26 and 28 are connected together by screws 30-30, with two spaced screws for each standoff member. Standoff members 26 and 28 are located adjacent opposing sides of the support plates, with one standoff member being positioned toward one orthogonal side adjacent and the other standoff member being positioned toward the other orthogonal side adjacent, as shown in FIGS. 3 and 4 most clearly. This specific arrangement could be varied, however. In the embodiment shown, support plates 22 and 24 and the standoff members 26 and 28 are made from a hard plastic.

A plastic sleeve 20 is coupled to the eccentric portion 18 of the motor shaft, so that sleeve 20 rotates with action of the motor shaft. Extending also between support plates 22 and 24 and rotatable therein is a brushhead shaft 32. Attached fixedly to brushhead shaft 32 between support plates 22 and 24 and positioned longitudinally in line with sleeve 20 along brushhead shaft 32 is a yoke member 36. Secured to and between a free end 35 of sleeve 20 and a free end 37 of yoke member 36 is a spring member 38. Spring member 38 is a compression spring in the embodiment shown which, in one position, shown in FIG. 3, is compressed, and in another position, shown in FIG. 4, is released (extended), which occurs alternately as motor shaft 16 rotates. The sleeve 20 alternately compresses and releases spring 38 as the motor shaft rotates. Spring 38 has a spring rate of 10-30 Newtons/mm, preferably approximately 18.8 Newtons/mm. In the embodiment shown in FIGS. 1 and 2, brushhead shaft 32 is shown in two parts, the proximal part extending between and supported by the two support plates 22 and 24, while the distal part, onto which a brushhead 38 is removably connected, extends away from support plate 24. At the distal end of brushhead assembly 40 is a set of bristles 42.

In operation, spring 38 acts as a link between the eccentric portion 18 of motor shaft 16 and the brushhead shaft 32. When operated at the correct frequency, the excited spring operates to produce a sweeping alternating motion of brushhead shaft 32. In the embodiment shown, the angle of motion is between 6°-18°, while the frequency is between 150-300 Hz. The sweeping action is produced by the action of the spring 38 on yoke 36. The distance between the spring/yoke connection and the axis of the brushhead shaft is referred to as a moment arm. The moment arm in the embodiment shown is preferably 7.5 mm long, but can vary between 2 and 15 mm.

The drive train shown in operation uses a mechanical excitation of spring member 38, to produce a resonant response of the spring member and the brushhead near to or at the resonant frequency of the dynamic system. The force generated by the plastic sleeve 20 by means of the rotating eccentric shaft excites spring 38. At the distal end of spring 38, the force applied to the moment arm provides the required torque to the brushhead shaft to produce the sweeping motion of the brushhead assembly 40 and the bristles 42.

Depending upon the voltage supplied to DC motor 14, the stiffness of the spring member 38 and the inertia of the overall system, the desired resonant mode of the spring can be controlled. The amplitude of the bristle motion can be controlled by varying the eccentricity of the eccentric portion 18 of the drive shaft, the frequency of operation and the length of the moment arm. Amplitude is also affected by the moment of inertia of the oscillating components, including the brushhead shaft and the brushhead assembly.

In the arrangement of FIGS. 1-5, the spring member 38 serves two purposes; (1) it constrains the motion of the plastic sleeve 20 to a sweeping alternating motion (instead of a rotating action), which is effective for teeth cleaning, and (2) it facilitates the overall resonant frequency of the dynamic system. Depending upon the stiffness of the compression spring and the system inertia, the resonant frequency of the oscillating system for the sweeping motion can be adjusted.

Figure 6:
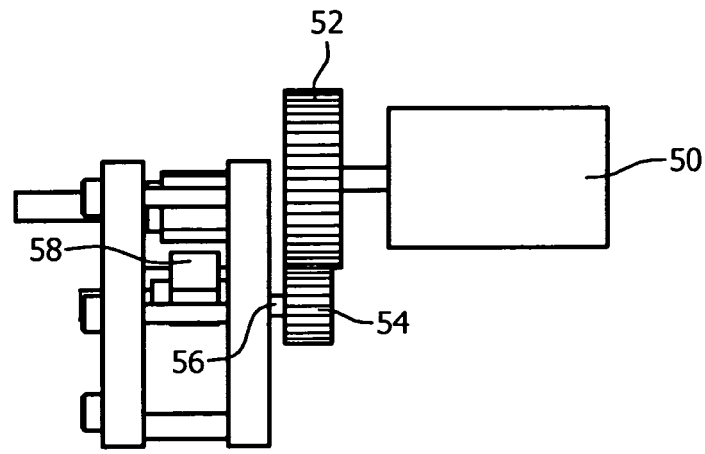
FIG. 6 is a side elevational view showing an alternative embodiment to that of FIGS. 1-5.

FIG. 6 shows an alternate embodiment, in which the toothbrush motor 50 motor drives a first gear 52 which in turn drives a mating gear 54 to which is mounted an eccentric shaft 56 on which a plastic sleeve 58 is positioned. With this drive train arrangement, it is possible to provide a lower cost toothbrush, primarily because the speed multiplying effect of the gear arrangement permits the use of a lower speed and hence lower cost motor. It may also be used to vary the frequency of the brushhead motion. The embodiment of FIG. 6, as with the other embodiments described above, is suitable for use in other personal care appliances, such as for instance electric shavers, which may require a different operating frequency.

Figure 7:
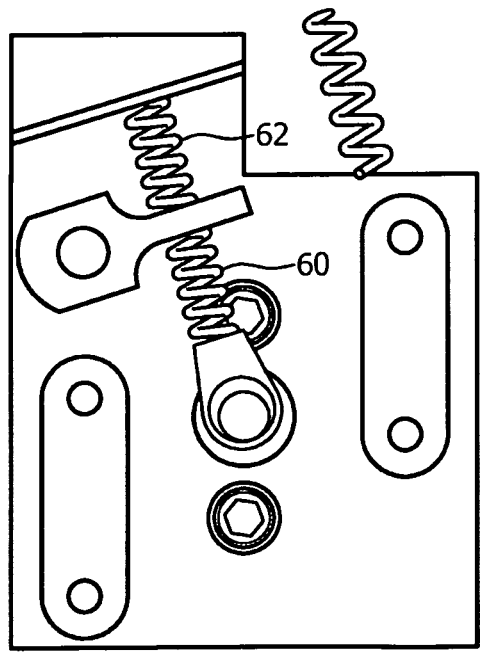
FIG. 7 is a cross-sectional view of an alternative embodiment to the spring arrangement of FIGS. 1-6.

FIG. 7 shows an alternative spring embodiment for the embodiments of FIGS. 1-6, includes two springs 60 and 62 in an otherwise similar drive train arrangement. The springs have a pre-load such that the two springs stay in some state of compression at all times, instead of alternating between compression and extension. This arrangement results in reduced fatigue and reduced noise for the appliance.

Hence, a drive train for a power toothbrush has been disclosed which uses a mechanical drive arrangement operating on a spring assembly, in which an eccentric portion of the drive shaft is used to excite the spring member and produce the desired resonant sweeping motion of the brushhead.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A power toothbrush, comprising:
a driving assembly, including a battery and a DC motor (14), the DC motor having a rotating drive shaft (16) extending therefrom, the drive shaft having a free end rotationally mounted in first and second spaced apart fixed support members (22, 24) wherein at least the first fixed support member is secured to a handle portion of the toothbrush, the drive shaft including an eccentric portion (18) located proximately from a proximal end thereof, extending outwardly from the drive shaft from between the first and second fixed support members, wherein the eccentric portion rotates with the drive shaft;
a spring assembly extending outwardly from the eccentric portion, the spring assembly including a spring member (38) which alternates between two conditions as the drive shaft rotates about an axis and the eccentric portion moves about said axis;
a brushhead shaft member (32), positioned laterally away from the driveshaft, extending between the fixed support members (22, 24) and rotatable therein, wherein the brushhead shaft member has a yoke member (36) secured thereto and extending away therefrom, wherein the spring member extends between the eccentric portion and the yoke member, wherein in operation, an oscillating action of the brushhead shaft is produced as the drive shaft rotates, with the spring member alternating between its two conditions; and
a brushhead assembly (40) with bristles (42) mounted on the brushhead shaft for cleaning a user's teeth.

2. The toothbrush of claim 1, wherein the spring member includes a single spring which in operation moves alternately between compression and extension.

3. The toothbrush of claim 1, wherein the spring assembly includes a plastic sleeve member (20) which is positioned on the eccentric portion, the plastic sleeve member having such a configuration that as the drive shaft of the motor rotates, the spring member moves between said two conditions.

4. The toothbrush of claim 1, wherein the DC motor has a speed within the range of 5,000-20,000 rpm and a torque within the range of 0.2-1.5 mNm.

5. The toothbrush of claim 1, wherein the spring has a spring rate in the range of 10 Newtons/mm to 30 Newtons/mm.

6. The toothbrush of claim 1, wherein there is a moment arm between the spring contact with the yoke member and the brushhead shaft axis, having a length in the range of 2-15 mm.

7. The toothbrush of claim 1, wherein the spring member includes two spring member portions (60, 62) connected so that two spring member portions are always in compression.

8. The toothbrush of claim 1, wherein the drive shaft includes a gear assembly (52, 54) prior to the eccentric portion, wherein changing the gear assembly produces a change in frequency of operation of the toothbrush and/or a change in the speed of the drive shaft.

* * * * *